(12) United States Patent
Chen et al.

(10) Patent No.: US 10,101,246 B2
(45) Date of Patent: Oct. 16, 2018

(54) METHOD OF PREPARING A PLAN-VIEW TRANSMISSION ELECTRON MICROSCOPE SAMPLE USED IN AN INTEGRATED CIRCUIT ANALYSIS

(71) Applicant: SHANGHAI HUALI MICROELECTRONICS CORPORATION, Shanghai (CN)

(72) Inventors: Qiang Chen, Shanghai (CN); Yanping Shi, Shanghai (CN)

(73) Assignee: SHANGHAI HUALI MICROELECTRONICS CORPORATION, Shanghai (CN)

( * ) Notice: Subject to any disclaimer, the term of this patent is extended or adjusted under 35 U.S.C. 154(b) by 0 days.

(21) Appl. No.: 15/241,284

(22) Filed: Aug. 19, 2016

(65) Prior Publication Data

US 2017/0053778 A1    Feb. 23, 2017

(30) Foreign Application Priority Data

Aug. 20, 2015 (CN) .......................... 2015 1 0514446

(51) Int. Cl.
*G01N 1/28* (2006.01)
*H01J 37/26* (2006.01)

(52) U.S. Cl.
CPC ............... *G01N 1/286* (2013.01); *G01N 1/28* (2013.01); *H01J 37/26* (2013.01); *H01J 2237/31745* (2013.01)

(58) Field of Classification Search
CPC ...... H01J 37/26; H01J 37/305; H01J 37/3065; H01J 2237/31745; H01J 2237/20; H01J 2237/31749
See application file for complete search history.

(56) References Cited

U.S. PATENT DOCUMENTS

| 6,570,170 B2* | 5/2003 | Moore | G01N 1/286 250/492.1 |
| 7,375,325 B2* | 5/2008 | Burkhardt | B25J 7/00 250/306 |
| 7,414,252 B2* | 8/2008 | Moore | B82Y 15/00 250/307 |

(Continued)

*Primary Examiner* — Wyatt Stoffa
(74) *Attorney, Agent, or Firm* — Tianchen LLC

(57) ABSTRACT

The present invention discloses a preparation method of plan-view TEM sample used in an integrated circuit analysis. The method comprises the steps of: providing a carrying slice, and fixing a chip containing a targeted structure sample and the carrying slice on a sample holder in a horizontal direction, and putting them in a process chamber of a FIB apparatus; cutting off a piece of chip structure containing a target structure sample by adopting a FIB; and welding the piece of chip structure on the flat and clean side of the carrying slice by using a nano-manipulator; after being taken out from the process chamber of the FIB apparatus, the carrying slice welded with the chip structure is adjusted to vertical direction, and is put in the process chamber of the FIB apparatus again; transferring and welding the chip structure on the TEM copper grid by using the nano-manipulator; and removing one layer or multiple layers above the preset target layer from the surface layer of the chip by using the FIB to obtain the desired plan-view TEM sample.

10 Claims, 7 Drawing Sheets

(56) References Cited

U.S. PATENT DOCUMENTS

| | | | | |
|---|---|---|---|---|
| 7,423,263 B2* | 9/2008 | Hong | G01N 1/32 | 250/304 |
| 8,258,473 B2* | 9/2012 | Shaapur | G01N 1/286 | 250/307 |
| 9,040,908 B2* | 5/2015 | Young | G01N 1/32 | 250/304 |
| 9,368,325 B2* | 6/2016 | Young | G01N 1/32 | |
| 2004/0004186 A1* | 1/2004 | Jiyan | G01N 1/286 | 250/307 |
| 2005/0037625 A1* | 2/2005 | Anciso | H01J 37/3056 | 438/712 |
| 2007/0272854 A1* | 11/2007 | Agorio | G01N 1/286 | 250/304 |
| 2008/0073535 A1* | 3/2008 | Hong | G01N 1/32 | 250/311 |
| 2010/0305747 A1* | 12/2010 | Agorio | G01N 1/286 | 700/213 |
| 2011/0006207 A1* | 1/2011 | Arjavac | G01N 1/32 | 250/307 |
| 2013/0340936 A1* | 12/2013 | Giannuzzi | H01J 37/20 | 156/330 |
| 2014/0084157 A1* | 3/2014 | Miller | H01J 37/3023 | 250/307 |
| 2014/0332699 A1* | 11/2014 | Coyle | G01N 1/32 | 250/492.3 |
| 2015/0001176 A1* | 1/2015 | Young | G01N 1/32 | 216/37 |
| 2015/0255250 A1* | 9/2015 | Sato | G01N 1/286 | 250/307 |
| 2015/0325409 A1* | 11/2015 | Young | G01N 1/32 | 250/492.3 |
| 2016/0064187 A1* | 3/2016 | Tomimatsu | H01J 37/3023 | 250/453.11 |
| 2016/0163508 A1* | 6/2016 | Iwaya | H01J 37/3005 | 204/192.33 |
| 2016/0189929 A1* | 6/2016 | Hammer | G01N 1/32 | 250/492.21 |

* cited by examiner

METHOD OF PREPARING A PLAN-VIEW TRANSMISSION ELECTRON MICROSCOPE SAMPLE USED IN AN INTEGRATED CIRCUIT ANALYSIS

CROSS-REFERENCE TO RELATED APPLICATION

This application claims the priority benefit of Chinese Patent Application Serial No. 201510514446.0, filed Aug. 20, 2016. All disclosure of the Chinese application is incorporated herein by reference.

FIELD OF THE INVENTION

The present invention generally relates to the field of integrated circuit manufacturing technology, more particularly, to a method of preparing a plan-view transmission electron microscope (TEM) sample used in an integrated circuit analysis.

BACKGROUND OF THE INVENTION

The development of the semiconductor integrated circuit is very rapid since it appears as a new generation electronic device. In recent twenty years, the semiconductor integrated circuit undergoes three development phases, from small scale, middle scale to large scale. At present, the semiconductor integrated circuit is developing toward to the very-large-scale integration (VLSI) phase, and the development and application thereof have become one of the most active and important fields in modern science and technology.

The semiconductor integrated circuit chip undergoes a plurality of complicated processes to stack layers of polycrystalline silicon, silicon oxide, and metal interconnection one by one; so as to connect countless devices together to achieve complicated functions. In the process of semiconductor integrated circuit chip designing and manufacturing, failure analysis and the like is very important. The chip designer can perform a targeted test for chip problems by the failure analyses so as to quickly and accurately verify the design scheme, and if there is a problem in a region of the chip, the region will be isolated so as to find the reason of the problem. It is needed to prepare a plan-view TEM sample before the failure analyses are performed.

The TEM is one of the most important instruments in research of material, and it is also be used in the fundamental research, development and application of the Nanotechnology. The characteristic of this technology is to directly cut out a film, which may be researched by TEM or high resolution electron microscopy, from a specimen in nanometer or micrometer dimensions. Another characteristic of this technology is not to damage the original structure of the specimen.

The TEM has been widely applied in various fields including the integrated circuit analysis and the application thereof becomes more and more important, while the sample prepared by Focused Ion Beam (FIB) is a major means of TEM sample preparation in the semiconductor field. In addition to cross-sectional TEM samples, it is mostly necessary to make a planar TEM analysis. At present, the preparation of the plan-view TEM sample is mainly completed by using FIB.

The FIB is to generate a secondary electron signal by irradiating the surface of the sample with an ion beam which is generated from a liquid metal (Ga) ion source, accelerated and focused by an ion gun, thus obtain an electron image. Such function is similar to that of SEM (Scanning electron microscope), or to complete the surface topography processing in micrometer or nanometer scale by stripping the surface atom with a strong current ion beam. Generally, metal, silicon oxide layer or metal deposition layer is selectively stripped by a physical sputtering method with a chemical gas reaction.

The flow of the plan-view TEM sample preparation in prior art is mainly as follows:

Firstly, lying a sample of the semiconductor integrated circuit chip on a platform, and making the cross section of the sample close to a target region by cleaving or polishing (as shown in FIG. 1);

Then, cutting a first plane (as shown in FIG. 2) and a second plane (as shown in FIG. 3) of the sample with FIB;

Finally, forming the TEM sample (as shown in FIG. 4).

It is clear for persons skilled in the art that, in reverse engineering analysis, for example, when the reverse engineering analysis is performed on a certain chip, it is needed to prepare a plan-view TEM sample in a certain region on the chip to analyze the structure such as polycrystalline silicon gate (Poly Gate), while the rest chip needs to be kept well so as to enable more region analysis later. However, the first step of the above process of preparing the plan-view TEM sample needs to cleave or polish the sample to an extent that the cross section of the sample is close to the target region, and this step will cause a large amount of region on the chip be completely removed, which will cause subsequence analyses difficult to perform or could not perform at all.

Therefore, how to obtain the planar TEM data in the target region while the rest of chip is not damaged, is a new challenge for people in this field.

BRIEF SUMMARY OF THE DISCLOSURE

The object of the present invention is to provide a preparation method of a plan-view TEM sample used in an integrated circuit analysis, and this method can conveniently prepare the plan-view TEM sample by using a carrying slice as a transition medium. The most importantly is that this method can prevent the rest of the chip from being severely damaged so as to provide a good condition for the subsequent various analyses.

In order to achieve the above object, the technical solution of the present invention is as follows:

A preparation method of a plan-view TEM sample used in an integrated circuit analysis, for exposing at least one of preset target regions of an integrated circuit chip with a multi-layer structure, wherein a targeted structure sample to be inspected is contained in the target region, the method comprises the following steps:

Step S1: providing a carrying slice, and fixing the integrated circuit chip containing the targeted structure sample and the carrying slice on a sample holder in a horizontal direction, and putting them in a process chamber of a focused ion beam apparatus, wherein the carrying slice has at least one flat and clean side;

step S2: cutting off a piece of chip structure containing the targeted structure sample by adopting a focused ion beam; and welding the piece of chip structure on the flat and clean side of the carrying slice by using a nano-manipulator; wherein each layer of the integrated circuit chip containing the targeted structure sample is vertical to the emission direction of the focused ion beam;

step S3: taking the carrying slice out from the process chamber of the focused ion beam apparatus, adjusting the carrying slice welded with the piece of chip structure to vertical direction, and putting in the process chamber of the focused ion beam apparatus again;

step S4: transferring and welding the piece of chip structure on a TEM copper grid by using the nano-manipulator;

Step S5: removing one layer or multiple layers above the preset target layer from the surface layer of the integrated circuit chip by using the focused ion beam to obtain the desired plan-view TEM sample, wherein each layer of the integrated circuit chip containing the targeted structure sample is parallel with the emission direction of the focused ion beam.

Preferably, when the carrying slice welded with the piece of chip structure, after being taken out from the process chamber of the focused ion beam apparatus, is adjusted to vertical direction and is put in the process chamber of the focused ion beam apparatus again in the step S3, the piece of chip structure is welded on the upper end of the flat and clean side of the carrying slice.

Preferably, the area of the piece of chip structure containing the targeted structure sample which is cut off in the target region by using the focused ion beam in the step S2, is in a range of 1 μm to 10 μm multiply by a range of 1 μm to 10 μm ((1 μm to 10 μm)*(1 μm to 10 μm)).

Preferably, the depth range of the target layer of the piece of chip structure containing the targeted structure sample, which is cut off in the target region by using the focused ion beam in the step S2, is from 1 μm to 5 μm.

Preferably, the material of the carrying slice is conductive material.

Preferably, the material of the carrying slice is silicon.

Preferably, the shortest distance from the cross section of the piece of chip structure containing the targeted structure sample, which is cut off in the step S2, to the target structure sample is in a range of 1 μm to 4 μm.

Preferably, the shape of the piece of chip structure containing the targeted structure sample, which is cut off in the step S2, is right triangle.

Preferably, the right-angle side of the piece of chip structure in a shape of the right triangle is welded together with the flat and clean side of the carrying slice.

Preferably, the preset target region is gate oxide layer, tungsten plug (CT) or metal layer.

It can be seen from the above technical solution, the present invention cuts out TEM sample only in the target region without causing the rest chip being severely damaged, by using the carrying slice as a transition medium, which is very suitable for cases have multiple analysis targets with limited number of chips, such as reverse engineering. The present invention can prepare the plan-view TEM samples conveniently, and most importantly, this method can prevent the rest of chip from being severely damaged so as to provide good condition for the subsequent various analyses; and this method can reduce the difficulty of the sample preparation and the analysis cost, and it is very effective to improve the analysis efficiency and quality.

DETAILED DESCRIPTION OF THE EMBODIMENTS

The specific embodiments of the present invention are described in detail below in combination with FIGS. 5-20. It shall be noted that, in order to satisfy the need of the subsequent detection methods, for example, in the embodiment of the present invention, at least one of preset target regions of the integrated circuit chip with a multi-layer structure is exposed, wherein a targeted structure sample to be inspected is contained in the preset target region, and the targeted structure sample may be exposed to the surface of a preset target layer, which can be understood to expose any one or more layers among the preset target layers of the integrated circuit chip with a multi-layer structure shown in FIG. 6, the preset target layers containing the target structure sample to be inspected. The preset target layer may be a gate oxide layer, CT, metal layer or the like.

In general, the multi-layer integrated circuit chip is rectangle or square, and the number of the cross section thereof is four. The difference from the prior art is that, in the embodiment of the present invention, the cross section polishing method (for example, chemical mechanical polishing, etching method or ion polishing method), which starts polishing from the cross section to be polished and stop at the position which is micrometer scale distance from the target structure sample, is not used. Instead, the FIB is used to cut off a piece of chip structure containing a targeted structure sample, and a carrying slice is used as a transition medium to transfer and weld the piece of chip structure on a TEM copper grid. Then a refined processing is performed on the chip structure on the TEM copper grid to obtain a desired plan-view TEM sample. For example, when a reverse engineering analysis is performed on a certain chip, it is necessary to prepare one plan-view TEM sample in a certain region on the chip to analyze the structure such as Poly Gate, while the rest chip is needed to keep well so as to conveniently perform analyses for more regions later.

Figure 1:
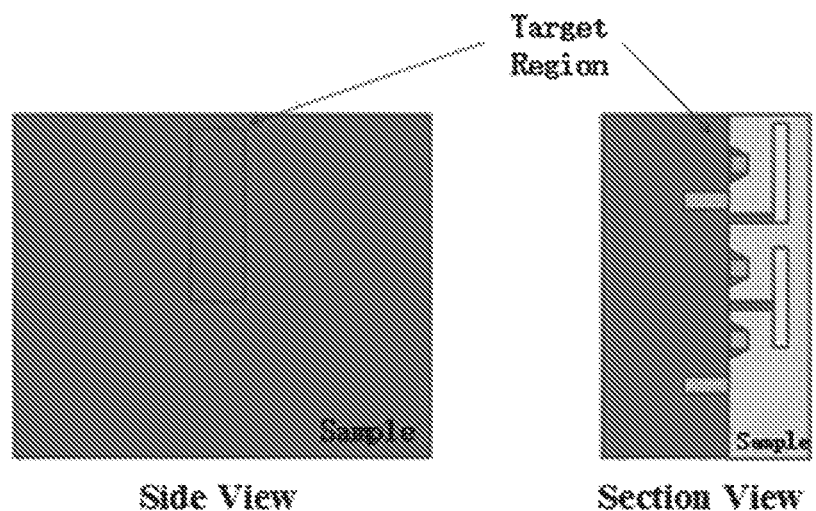
FIG. 1 is a schematic diagram of a structure of a sample, which at least has a preset target region, of a multi-layer integrated circuit chip in the prior art.
Figure 2:
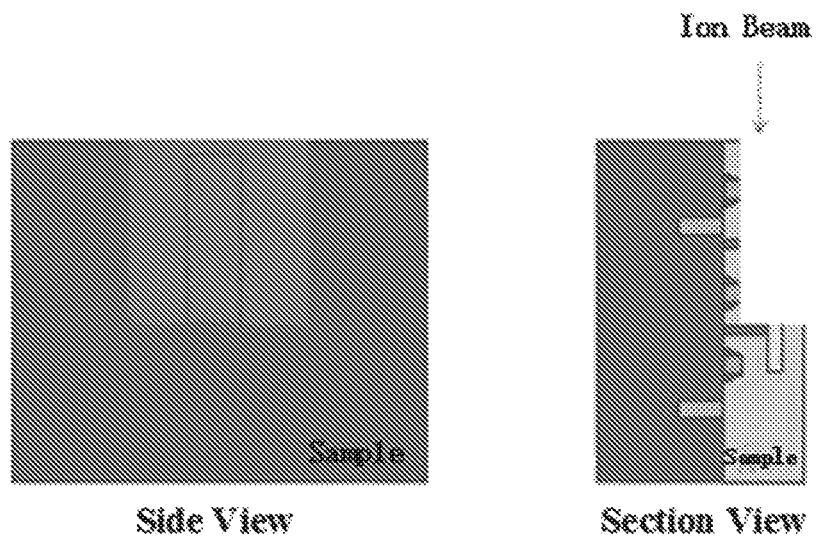
FIG. 2 is a schematic diagram of the structure of the TEM sample after the first plane is cut in the prior art.
Figure 3:
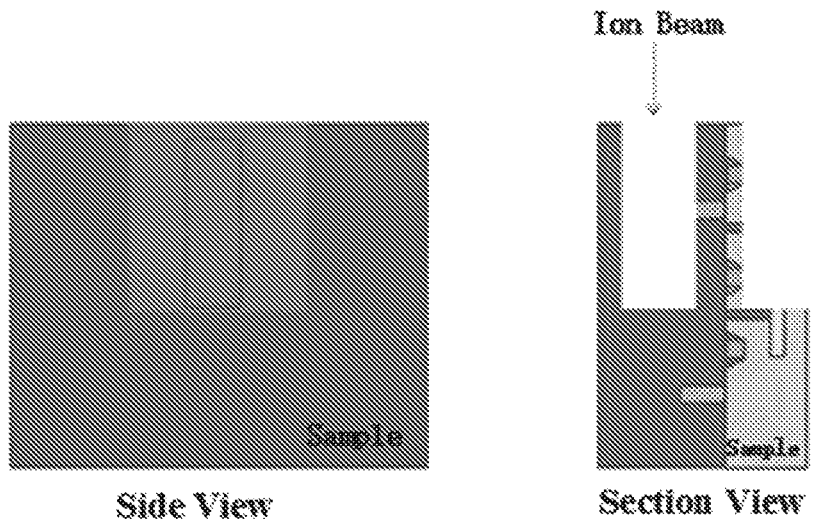
FIG. 3 is a schematic diagram of the structure of the TEM sample after the second plane is cut in the prior art.
Figure 4:
FIG. 4 is a schematic diagram of the structure of the completed TEM sample in the prior art.
Figure 5:
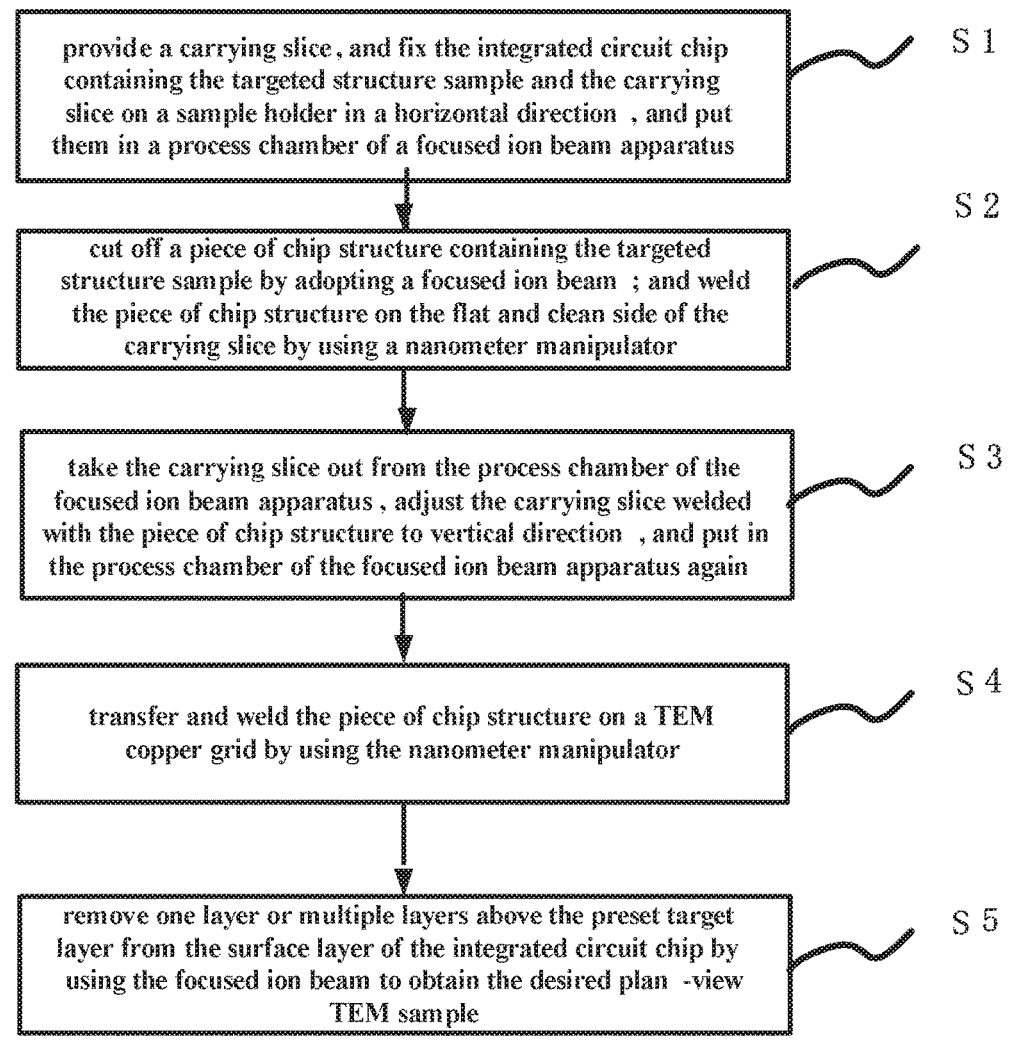
FIG. 5 is a schematic diagram of a flow of the preparation method of a plan-view TEM sample used in an integrated circuit analysis according to one embodiment of the present invention.
Figure 6:
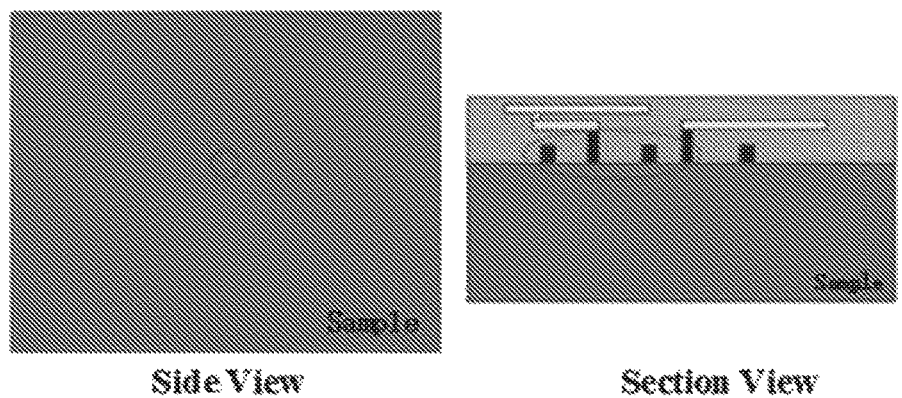
FIGS. 6-20 are schematic diagrams of the structure obtained after adopting each step of the preparation method of a plan-view TEM sample used in an integrated circuit analysis according to one embodiment of the present invention.

Hereinafter, in connection with FIG. 5, the embodiments of the present invention are described in detail by referring FIGS. 7-20. FIG. 5 is a schematic diagram of a flow of the preparation method of plan-view TEM sample used in the integrated circuit analysis according to one embodiment of the present invention; and FIGS. 7-20 are schematic diagrams of the structure obtained after adopting each step of the preparation method of plan-view TEM sample used in the integrated circuit analysis according to one embodiment of the present invention.

Figure 7:
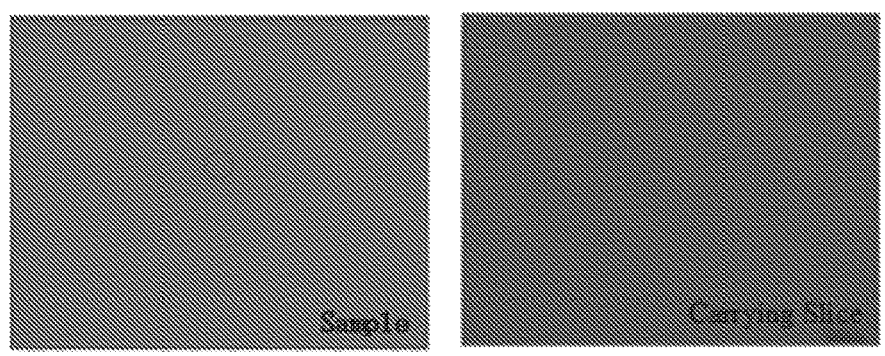

As shown in FIG. 5, the preparation method of plan-view TEM sample used in the integrated circuit analysis of the present invention may comprise the following steps:

Step S1: providing a carrying slice, and fixing an integrated circuit chip containing a targeted structure sample and the carrying slice on the sample holder in a horizontal direction (as shown in FIG. 7), and putting them in a process chamber of a FIB apparatus, wherein the carrying slice at least has one flat and clean side. Preferably, the material of the carrying slice is conductive material.

Figure 13:
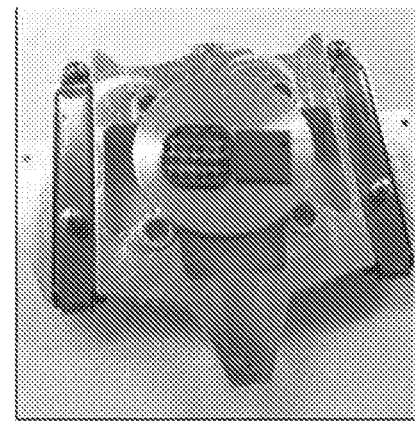

Specifically, the material of the carrying slice as a transition medium is conductive material, and more specifically, a general silicon wafer, such as a substrate made by the silicon material and the like. Please refer to FIG. 6 again; the targeted structure sample is located in upper portion of the integrated circuit chip. Before the preparation step, it is necessary to put the chip containing the targeted structure sample and the carrying slice horizontally in a process chamber of a FIB apparatus, that is, put them in a FIB sample holder (as shown in FIG. 13).

Figure 8:
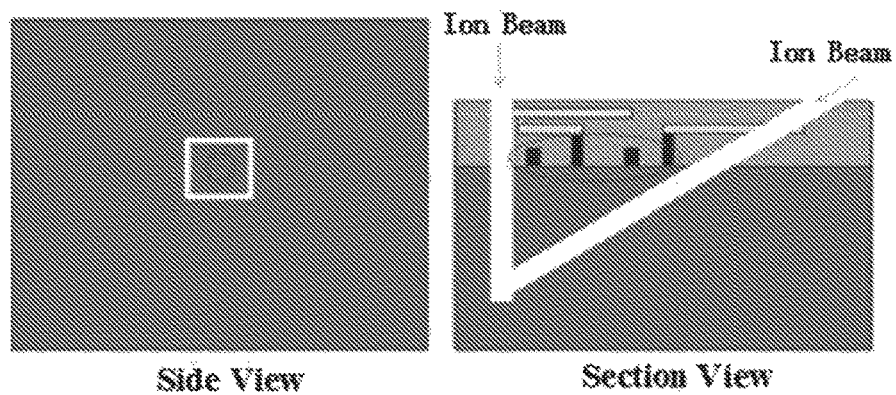
Figure 14:
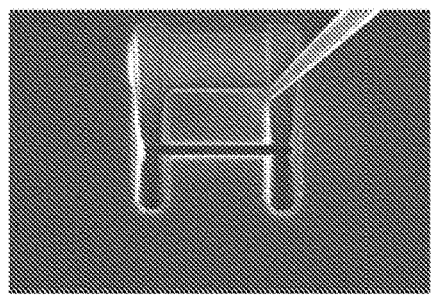

Next, the step S2 is performed: that is, cutting off a piece of chip structure containing the targeted structure sample by performing a focused ion beam (as shown in FIG. 14); wherein during cutting, each layer of the integrated circuit chip containing the targeted structure sample is vertical to the emission direction of the focused ion beam. The shape of the piece of the chip structure could be various; the triangle shape is preferred since it is convenient for cutting. Preferably, the shape of the piece of the chip structure containing the targeted structure sample cut off in the step S2 is right triangle (as shown in FIG. 8).

In general, the area of the piece of chip structure containing the target structure sample, which is cut off in the target region by using the focused ion beam may be in a range of 1 μm to 10 μm multiply by a range of 1 μm to 10 μm ((1 μm to 10 μm)*(1 μm to 10 μm)), and the depth range of the target layer of the chip structure may be from 1 μm to 5 μm.

Figure 9:
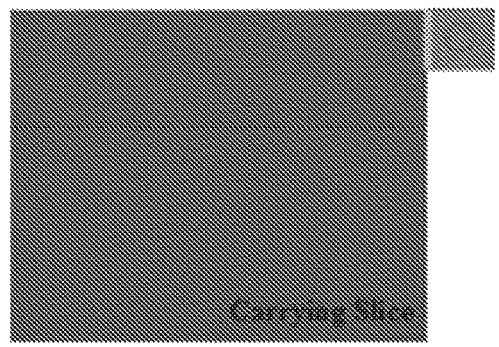
Figure 15:
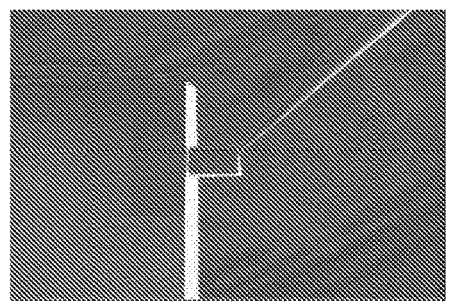

Then, the piece of chip structure is welded on the flat and clean side of the carrying slice by using a nano-manipulator, as shown in FIGS. 9 and 15. The piece of chip structure is right triangle, and the right-angle side of the right-triangle shaped chip structure is welded together with the flat and clean side of the carrying slice.

Figure 10:
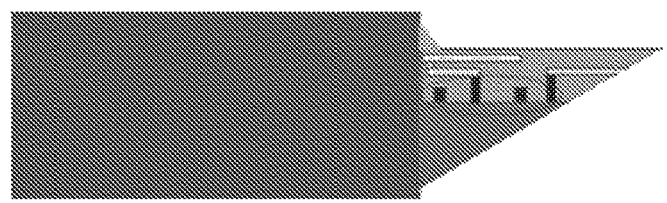

After the above steps have been completed, the step S3 is performed: taking the carrying slice out from the process chamber of the FIB apparatus, adjusting the carrying slice welded with the chip structure to vertical direction, and putting in the process chamber of the FIB apparatus again (as shown in FIG. 10).

Figure 16:
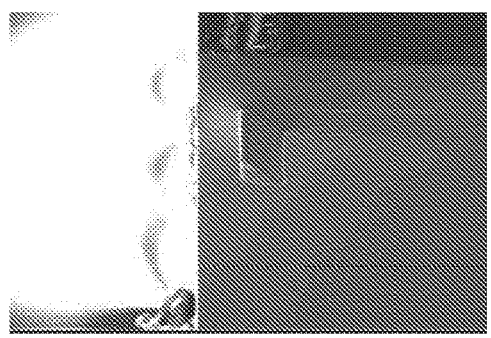

Further, the step S4 is performed: transferring and welding the piece of chip structure on a TEM copper grid by using the nano-manipulator, as shown in FIGS. 10 and 16.

Figure 11:
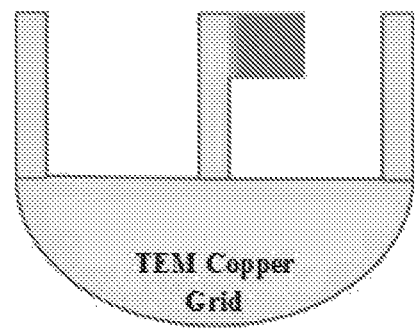
Figure 12:
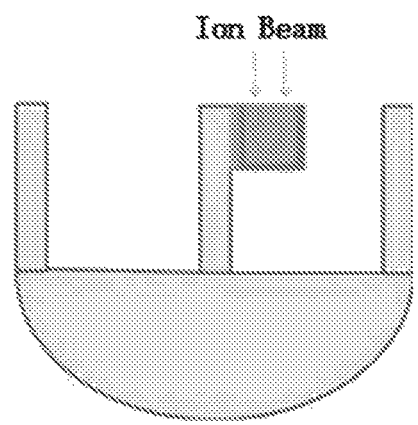
Figure 17:
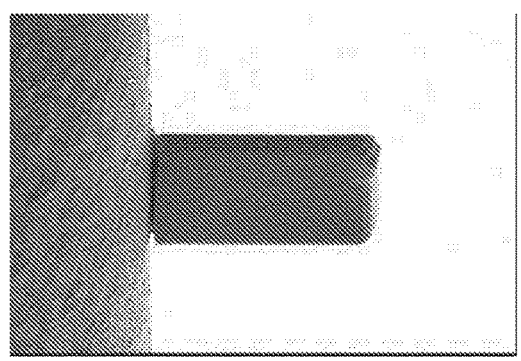
Figure 18:
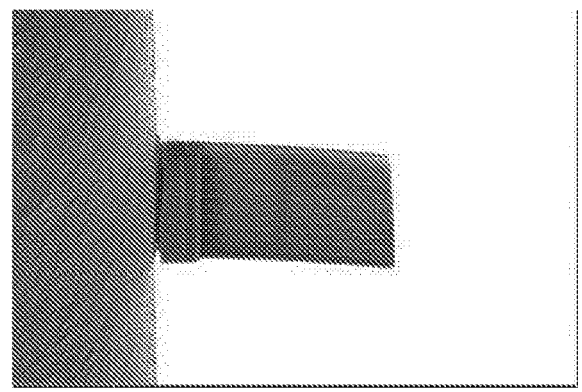
Figure 19:
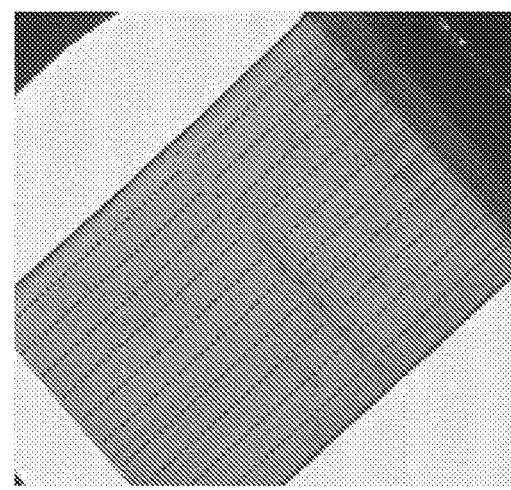
Figure 20:
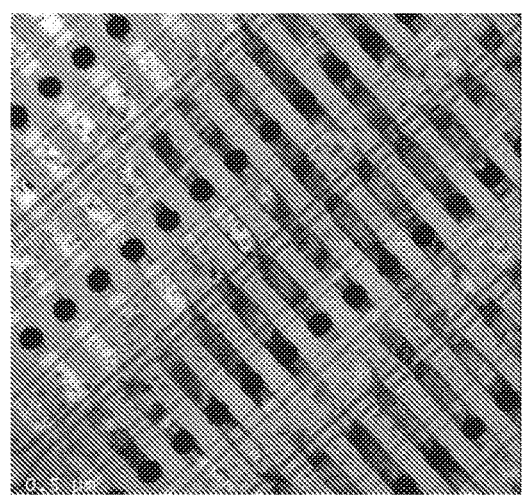

Step S5: removing one layer or multiple layers above the preset target layer from the surface layer of the integrated circuit chip, and at this time, each layer of the integrated circuit chip containing the targeted structure sample is parallel with the emission direction of the focused ion beam, as shown in FIGS. 11, 17 and 18. And the desired plan-view TEM sample is obtained (as shown in FIGS. 19 and 20). FIG. 19 shows the picture of the plan-view TEM sample prepared in the embodiment of the present invention with a small zoom-in ratio, and FIG. 20 shows the picture the plan-view TEM sample prepared in the embodiment of the present invention with a large zoom-in ratio.

In summary, the present invention can prepare the plan-view TEM sample conveniently by adopting the carrying slice as a transition medium, and most importantly, this method can prevent the rest of the chip from being severely damaged so as to provide good condition for the subsequent various analyses; in addition, for the reverse engineering analysis of the chip, this method can reduce the difficulty of the sample preparation and the analysis cost, and improve the analysis efficiency and quality.

While this invention has been particularly shown and described with references to preferred embodiments thereof, if will be understood by those skilled in the art that various changes in form and details may be made herein without departing from the spirit and scope of the invention as defined by the appended claims.

The invention claimed is:
1. A preparation method of plan-view TEM sample used in an integrated circuit analysis, for exposing at least one of preset target regions of an integrated circuit chip with a multi-layer structure, wherein the at least one of preset target regions contains a targeted structure sample to be inspected, wherein the preparation method comprising the following steps:
   Step S1: providing a carrying slice, and fixing the integrated circuit chip containing the targeted structure sample and the carrying slice spaced from each other on a sample holder along a horizontal axis, and putting them in a process chamber of a focused ion beam apparatus, wherein the carrying slice has at least one flat and clean side;
   step S2: cutting off a piece of the integrated circuit chip containing the targeted structure sample by adopting a focused ion beam; and welding the piece of the integrated circuit chip on the flat and clean side of the carrying slice by using a nano-manipulator; wherein the focused ion beam is perpendicular to a top surface of each layer of the integrated circuit chip containing the targeted structure sample;
   step S3: taking the carrying slice out from the process chamber of the focused ion beam apparatus, then adjusting a direction of the carrying slice welded with the piece of the integrated circuit chip such that the focused ion bean is parallel to the top surface of each layer of the integrated circuit chip containing the target structure sample, and putting the carrying slice welded with the piece of the integrated circuit chip into the process chamber of the focused ion beam apparatus again;
   step S4: transferring and welding the piece of the integrated circuit chip on a TEM copper grid by using the nano-manipulator;
   Step S5: removing one layer or multiple layers above the preset target region from a top surface layer of the integrated circuit chip by using the focused ion beam to obtain the plan-view TEM sample, wherein the focused ion beam is parallel with the top surface of each layer of the integrated circuit chip containing the targeted structure sample.

2. The preparation method according to claim 1, wherein when the carrying slice welded with the chip structure, after being taken out from the process chamber of the focused ion beam apparatus, is adjusted and is put in the process chamber of the focused ion beam apparatus again in the step S3, the piece of the integrated circuit chip welded on a top end of the flat and clean side of the carrying slice.

3. The preparation method according to claim 1, wherein the piece of the integrated circuit chip containing the targeted structure sample, which is cut off in the target region by using the focused ion beam in the step S2, is square with a side length in a range from 1 μm to 10 μm.

4. The preparation method according to claim 1, wherein a thickness of the piece of the integrated circuit chip containing the targeted structure sample, which is cut off in the target region by using the focused ion beam in the step S2, is in a range from 1 μm to 5 μm.

5. The preparation method according to claim 1, wherein the material of the carrying slice is conductive material.

6. The preparation method according to claim 5, wherein the material of the carrying slice is silicon.

7. The preparation method according to claim 1, wherein the shortest distance from a top surface of the piece of the integrated circuit chip containing the targeted structure sample, which is cut off in the step S2, to a top surface of the target structure sample is in a range from 1 μm to 4 μm.

8. The preparation method according to claim 1, wherein a horizontal projection shape of the piece of the integrated circuit chip containing the targeted structure sample, which is cut off in the step S2, is a right triangle.

9. The preparation method according to claim 8, wherein a leg of the piece of right triangle shaped integrated circuit chip is welded together with the flat and clean side of the carrying slice.

10. The preparation method according to claim 8, wherein the preset target region is a gate oxide layer, a contact hole layer or a metal layer.

* * * * *